United States Patent [19]
Milberger et al.

[11] 3,937,065
[45] Feb. 10, 1976

[54] DELAMINATION DETECTOR
[75] Inventors: Lionel J. Milberger; Gilbert Swift, both of Bryan; William M. Moore, College Station, all of Tex.
[73] Assignees: William Moore; G. Swift, both of College Station, Tex.
[22] Filed: June 12, 1973
[21] Appl. No.: 369,187

Related U.S. Application Data
[62] Division of Ser. No. 176,906, Sept. 1, 1971, Pat. No. 3,762,496.

[52] U.S. Cl............................................... 73/67; 73/67.7
[51] Int. Cl.² .................................................. G01N 29/04
[58] Field of Search................ 73/67, 70, 69, 67.8 R, 73/67.8 S, 67.5, 67.7, 556, 552, 555; 181/.5 AC, .5 NP, .5 EC, .5 VH, 114

[56] References Cited
UNITED STATES PATENTS
3,224,253  12/1965  McKay.................................. 73/67
3,361,225  1/1968   Nichols............................... 73/67 X
3,531,983  10/1972  Heath et al. ....................... 73/67.2
3,550,434  12/1970  Schroeer et al..................... 73/67.2
3,564,903  2/1971   Woodmansee et al. ............. 73/67.2
3,631,714  1/1972   Cressman ......................... 73/67.8 S X Primary Examiner—Donald O. Woodiel
Assistant Examiner—Stephen A. Kreitman

[57] ABSTRACT
To detect the presence of certain types of hidden flaws within a material having an exposed surface, the surface is tapped at one location to produce sonic vibrations within the material. At another location, an acoustic receiving transducer is coupled to the surface of the material being tested. A characteristic of the electrical signals produced by the transducer which is indicative of the type of flaw to be detected is utilized to denote the presence of a flaw. A mobile form of apparatus which detects flaws while traversing the surface of the material and which indicates the location as well as the existence of the flaws is described.

9 Claims, 5 Drawing Figures

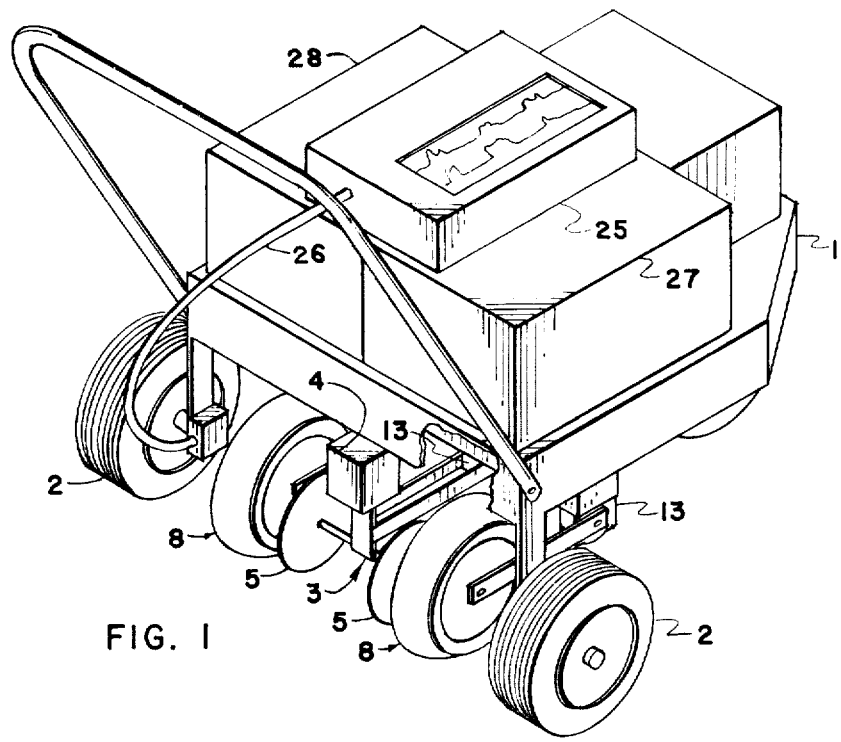
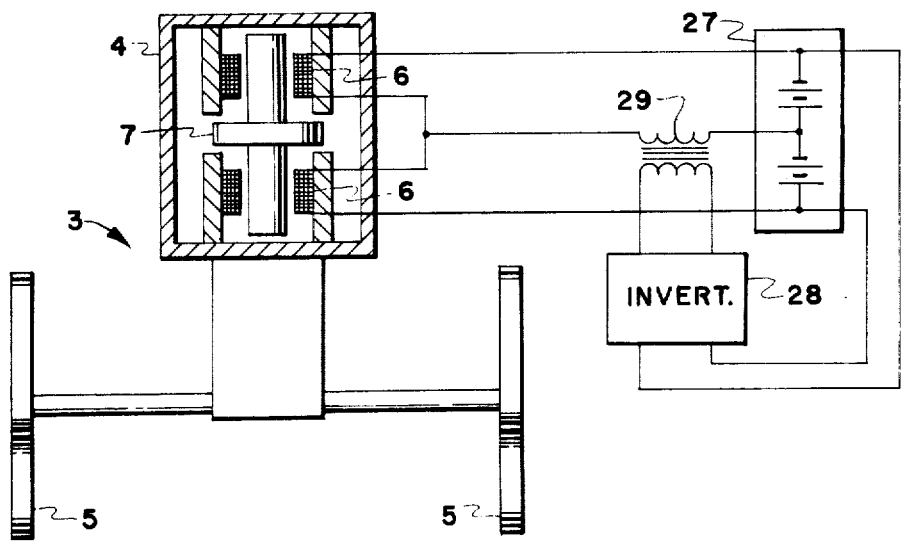

DELAMINATION DETECTOR

This is a division of application Ser. No. 176,906 now U.S. Pat. No. 3,762,496.

The present invention relates to a method and apparatus for detecting the presence of hidden flaws within a concrete bridge deck or other mass of material. The type of flaw which it is desired to detect consists of a separation of the material beneath the surface into two or more layers, or the presence of a lack of bond between two or more layers of a laminated material. Such separations are commonly called delaminations and the zones on the surface beneath which they occur are called delaminated areas. Delamination is one of the more commonly occurring defects in concrete bridge decks. It is encountered most frequently in localities where freeze-thaw conditions prevail during some portion of the year. As a consequence of becoming delaminated the concrete bridge deck deteriorates rapidly to the point of requiring extensive repair or replacement. Early detection of the delaminated areas permits remedial action to be applied at these areas in time to prevent the further progress of the deterioration and thus contributes to more economical bridge maintenance.

A similar form of separation occurs in rocks which form the ceiling of mine passages and tunnels. The safety of persons within these spaces is endangered by the presence of such flaws since the flaws tend to grow larger and eventually result in a fall of rock from overhead. Accordingly, it is desirable both on bridge decks and tunnel ceilings to detect and to map out the delaminated areas and to repeat this process from time to time in order to evaluate the growth, if any, of these areas.

Another similar form of delamination occurs in laminated structural forms like the honeycomb panels often used in aircraft construction and in plywood. A fabrication problem in such laminates is that of securely bonding the layers. Lack of bonding produces weak points in the laminates and can result in serious structural failure.

In the past, detection of delamination has been accomplished by tapping the exposed surface of the suspected material with a rod, hammer, or similar striking object while listening with the ear for a distinctive type of sound which has been found to occur when the material is delaminated beneath the tapped area. This characteristic sound is generally described as a "hollow" sound. The reliability of this subjective method of detection leaves much to be desired since it depends greatly upon the experience and judgement of the observer and is also highly dependent upon the characteristics of the object used to perform the tapping. Sticks and rods, for example produce a sound related to their own mass and length regardless of what material they are tapped against and this sound often overshadows the sound produced by the delaminated material. A steel ball-like mass tied at the end of a soft rope has been found to produce very little sound when struck against a solid deck but to produce a loud distinctive sound when struck against a delaminated area. A mobile device, developed by the Research Department of the Kansas State Highway Commission, strikes the deck at regular intervals with small wooden blocks. This device permits surveying large areas quickly; however, the wooden blocks are somewhat resonant which impairs interpretation. Nichols, U.S. Pat. No. 3361225 describes a metal pegged wheel, an acoustic pickup on the handle eliminates subjective judgement; however, this type of mechanism generates a large amount of signal on bonded panels and hence has poor contrast between bonded and unbonded areas.

Accordingly, with these difficulties and shortcomings in mind the present invention was conceived. Basically, the invention operates by repetitively tapping the surface of the material in a controlled uniform manner and by coupling an acoustic receiving transducer to the surface of the material a small fixed distance away from the point at which it is being tapped. This distance is chosen in relation to the minimum size of the delaminated area which it is desired to detect, since, for most reliable detection, both the tapping point and the receiving point should be within the surface area beneath which the delamination extends. A certain finite spacing is important to eliminate from the receiving transducer output a large component of signal which would be present if the receiving transducer were to be directly coupled to the tapping mechanism. This large component of signal would exist whether or not the material were delaminated and would impair, if not overshadow, the response of the receiving transducer to the presence of the delamination. Accordingly, spacings from as close together as two separate mechanisms can be put into contact with the surface without touching one another, which spacings are of the order of one or two inches, up to spacings of several feet may be used. With a spacing of two inches the device can detect delaminated areas as small as two inches in width. If a spacing of two feet is used the detected areas will in general extend across a width of two feet or more. Provisions are also made in the design of the apparatus to minimize the response of the receiving transducer to sound waves arriving through the air or through the framework of the apparatus which supports and maintains the tapping mechanism and the receiving transducer in contact with the surface being tested. The apparatus is designed to maintain contact with the surface and to operate continuously while progressing along the surface of the material being tested.

It is an object of the invention to provide an improved method and apparatus for detecting and automatically indicating the presence of delamination beneath the surface of a material.

It is another object to automatically record the relative magnitude and the position of delaminated areas along a path of travel along a surface.

It is a further object to provide a method and apparatus which responds to delamination without having appreciable response to external noise, or to other surface effects such as the roughness of the surface of the material.

It is a still further object to provide an improved method and apparatus for the detection of delamination in a mobile manner while traversing the surface of the material.

How these various objects are achieved by the method and apparatus of the present invention will become apparent when the following description is read in conjunction with the drawings in which—

FIG. 1 is a pictorial view of one embodiment of the present invention.

FIG. 2 is a diagrammatic view illustrating the details of the tapping assembly.

Figure 3:
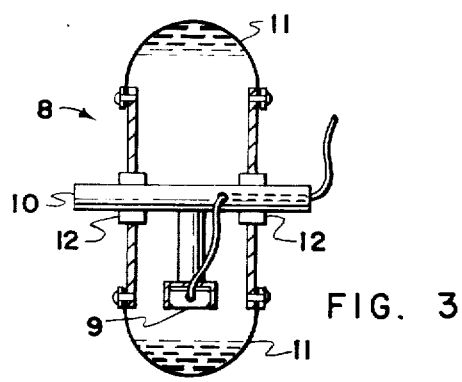
FIG. 3 is a sectional view showing the construction of the acoustic receiver wheel.

The device, as shown in FIG. 1, comprises a small three-wheeled cart 1, which forms a support and carriage for the other portions of the apparatus. Beneath the cart 1, in line with its rear support wheels 2, a tapping assembly 3 having two steel wheels 5 is supported in rolling contact with the surface of the material to be tested. An electrically operated vibrator mechanism 4 causes the two steel wheels 5 of the tapping assembly 3 to chatter against the surface of the material being tested. The vibrator mechanism 4, as shown in FIG. 2, comprises a pair of solenoid coils 6 which alternately raise and lower a magnetic core 7 which strikes violently against a stop at each end of its travel. The solenoid coils 6 are biased with direct current from battery 27 and are energized with 60 cycles per second alternating current from inverter 28 through transformer 29 to maintain the oscillatory hammer-like action of the magnetic core 7. As a result of this repetitive vibration the entire tapping assembly 3 is lifted out of contact with the surface sixty times each second. It returns each time to strike the surface at the points of contact of its steel wheels 5 with the surface of the material being tested. Although other types of tapping mechanisms were found to be satisfactory, for example, a motor driven tapper, or even a rolling spur gear, the above described mechanism was found to best excite the characteristic hollow sound.

Two acoustic receiver wheels 8 are also supported from the cart, in line with rear support wheels 2, each wheel spaced a few inches away from one of the tapping wheels 5. Referring now to FIG. 3, the acoustic receiving wheels 8 each contain an acoustic receiving transducer 9 which is mounted to a fixed axle 10 and thereby held at a substantially fixed height above the surface. The receiving wheels 8 are liquid-filled to provide good acoustic coupling between the transducer 9 and the surface being tested and are equipped with thin inner-tube like rubber tires 11 which conform to any surface irregularities and maintain good acoustic coupling. The wheel 8 is free to rotate while the axle 10, which passes through sealed bearings 12, is maintained in fixed orientation so that the transducer 9 is always in close proximity to the surface. A transducer mounted directly on the axle of a solid aluminum wheel having a thin rubber tread was also found to make a satisfactory receiving wheel; however, it did not minimize the surface texture noise effects as well as the liquid filled receiving wheel described.

It will be apparent that acoustic vibrations introduced into the material by the tapping action of wheels 5 will be received from the material by the transducers 9. However, it is also apparent that vibrations might travel through the frame and supporting members of the cart 1 from the tapping assembly 3 to the transducers 9 within the receiving wheels 8. Coupling of this nature is avoided by isolating the tapping assembly 3 from the cart 1 and separately isolating the receiving wheels 8 from the cart 1 by means of vibration isolators 13. Acoustic coupling through the air between the tapping assembly 3 and the receiving transducers 9 is minimized by having transducers 9 immersed in liquid which, through the thin rubber tire 11, is well coupled to the surface of the material being tested.

Response of the transducers 9 to surface roughness and to motion of the apparatus along the surface is minimized with respect to their response to the presence of delamination by accepting only those portions of the electrical signals produced by the receiving transducers 9 which meet specific criteria. These criteria are adjustable, but it has been found optimum, when using the apparatus on concrete bridge decks, to accept only signals which occur during the first 3 milliseconds after the surface has been tapped, and of these signals only those frequency components which fall between 300 and 1200 Hertz.

Figure 4:
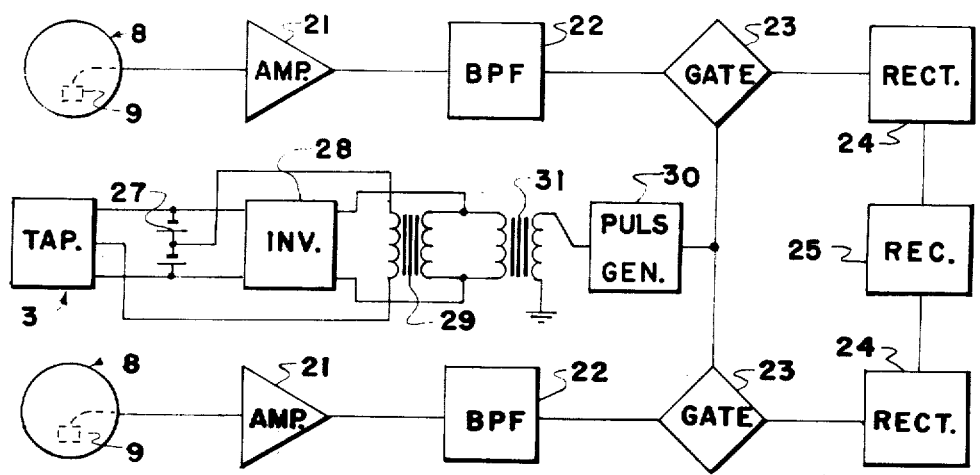
FIG. 4 is a block schematic diagram of the electronic signal processing portions of the apparatus.
Figure 5:
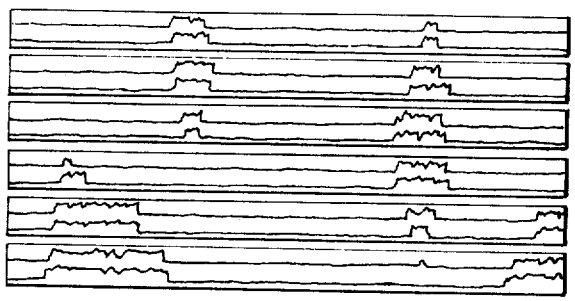
FIG. 5 is a typical set of successive recordings, made along parallel paths, placed side by side to form a visual map of the delaminated areas detected by the apparatus.

Thus, there is only a brief period after each tap during which the transducers 9 are allowed to influence the indications derived from their response. This fact tends to greatly suppress all unwanted types of response which are of a sustained nature. As shown in FIG. 4, the signals from the receiving transducers 9 are processed in conformance with the foregoing requirements by passing them separately through individual electronic amplifiers 21. Each amplifier 21 is associated with a filter 22 which passes only frequencies between 300 and 1200 Hz. The output of each filter 22 is blocked by a gate 23 which is opened by a pulse from pulse generator 30 for a brief interval synchronized with the action of the tapper 3 by a voltage from transformer 31. Transformer 31 is energized along with transformer 29 by inverter 28. The signals passing through gates 23 are rectified by rectifiers 24 to produce two uni-polar output voltages proportional to the respective magnitudes of the processed transducer signals. These two output voltages can be displayed on indicating meters to signify the presence and magnitude of any detected delamination, but in the more customary apparatus a pen-recorder 25 having right and left recording channels is used to produce a permanent-record of these voltages. The chart paper of the recorder 25 is driven in proportion to distance traversed by the cart through an odometer mechanism 26 driven by one of the supporting wheels 2. Thus, upon traversing a bridge-deck with the cart 1, a strip-map showing any delaminated areas encountered along this particular traverse is produced on the chart of recorder 25. As shown in FIG. 5, a succession of such records, with each traverse offset laterally a given distance, may be placed side by side to provide a visual map of the deck indicative of the size and position of the detected areas.

Power for operating the apparatus is obtained from a storage battery 27 and an inverter 28 which converts the 12 volt direct current of the battery to alternating current of 115 volts at 60 Hz. Thus, the entire apparatus is self-contained and is operable in remote locations while moving as well as while standing still.

The invention having been described, what is claimed is:

1. The method of detecting sub-surface flaws in a material comprising:
   Applying a repetitive tapping force to the surface of the material at selected locations,
   detecting on said surface at a point removed from the point of application of said force, an acoustic response related to said force and related to the acoustic characteristics of the flaw to be detected,
   producing, by time gating and frequency filtering of said detected response, an indication which is related to the distinguishing characteristics of the flaws to be detected, and whereby extraneous effects are diminshed, said time gating admitting only the initial portion of the acoustic response produced by each individual application of the repetitive tapping force.

2. The method set forth in claim 1 wherein the tapping force is applied approximately sixty times per second.

3. The method set forth in claim 1 wherein only the frequency components of the acoustic response which fall between 300 and 1200 Hz are utilized.

4. The method set forth in claim 3 wherein only that portion of the acoustic response which occurs during the first 3 milliseconds after a tapping force is utilized.

5. The method set forth in claim 4 wherein the acoustic response is rectified and integrated over a period of approximately ½ second.

6. The method of detecting sub-surface flaws in a material set forth in claim 1, wherein the applying of the tapping force and the detecting of an acoustic response is accomplished while in motion.

7. The method set forth in claim 6 wherein the indication produced is related to the distance traveled from a reference location.

8. The method for detecting subsurface delaminations and flaws in a material comprising:
   applying to the surface of the material sharp, short duration, repetitive, force impulses having sufficient energy to excite therein vibrations which are characteristic of the separation of the material into two or more unbonded layers,
   acoustically coupling a receiving transducer to the surface of the material to receive said characteristic vibrations at a location spaced from the application point of the force impulses, said spacing being comparable with the dimension of the minimum area of a delamination or flaw which it is desired to detect,
   producing an indication related to the magnitude of the response of said transducer to those frequency components of said characteristic vibrations, which fall between 300 and 1200 Hz.

9. The method set forth in claim 8 in which time gating and frequency filtering are used to obtain an indication which is related to the distinguishing characteristics of the flaws to be detected, and whereby extraneous effects are diminished.

* * * * *